US012569277B2

(12) United States Patent
Greenstein

(10) Patent No.: US 12,569,277 B2
(45) Date of Patent: Mar. 10, 2026

(54) INTRAOSSEOUS CATHETER PLACEMENT CONFIRMATION DEVICE AND METHOD

(71) Applicant: Sabra Medical, Inc., Westfield, NJ (US)

(72) Inventor: Yonatan Greenstein, Westfield, NJ (US)

(73) Assignee: Sabra Medical, Inc., Westfield, NJ (US)

( * ) Notice: Subject to any disclaimer, the term of this patent is extended or adjusted under 35 U.S.C. 154(b) by 995 days.

(21) Appl. No.: 17/724,859

(22) Filed: Apr. 20, 2022

(65) Prior Publication Data

US 2022/0338752 A1     Oct. 27, 2022

Related U.S. Application Data

(60) Provisional application No. 63/178,175, filed on Apr. 22, 2021.

(51) Int. Cl.
*A61B 17/34*     (2006.01)
*A61B 5/00*     (2006.01)
(Continued)

(52) U.S. Cl.
CPC ...... *A61B 17/3472* (2013.01); *A61B 5/02116* (2013.01); *A61B 5/03* (2013.01); (Continued)

(58) Field of Classification Search
CPC ............ A61B 2090/064; A61B 5/0215; A61B 5/7425; A61B 17/3401; A61B 5/032; (Continued)

(56) References Cited

U.S. PATENT DOCUMENTS 5,868,711 A * 2/1999 Kramer .............. A61B 17/3472
                                                      604/506
8,100,834 B2 * 1/2012 Shuler ................ A61B 5/14557
                                                      600/483

(Continued)

FOREIGN PATENT DOCUMENTS

WO     WO-2011022073 A1 * 2/2011    .......... A61B 5/0215
WO       2013003885 A2    1/2013
(Continued)

OTHER PUBLICATIONS

Compass, Available online at https://www.medline.com/product/Compass-Central-Venous-Pressure-Monitoring-Kit-by-Centurion/Z05-PF183126, manufactured by Centurion Medical Products. 1 page. Downloaded Jul. 20, 2022.

(Continued)

*Primary Examiner* — Wesley G Harris
(74) *Attorney, Agent, or Firm* — Hamilton, Brook, Smith & Reynolds, P.C.

(57)     ABSTRACT

A portable device is configured to connect directly to an intraosseous (IO) catheter and provide a clinician with actionable information to determine whether the catheter is placed correctly, such as whether the catheter is placed in the medullary cavity of bone. The device provides this information leveraging the presence or absence of arterial pressure waveforms. A method for assessing placement of an intraosseous catheter includes coupling a pressure transducer to an IO catheter placed in tissue, obtaining a continuous pressure waveform from a pressure signal provided by the pressure transducer, and assessing placement of the catheter based on the continuous pressure waveform.

15 Claims, 8 Drawing Sheets

(51) Int. Cl.
   *A61B 5/021*        (2006.01)
   *A61B 5/03*         (2006.01)
   *A61B 5/06*         (2006.01)
   *A61B 90/00*        (2016.01)
(52) U.S. Cl.
   CPC ............ *A61B 5/065* (2013.01); *A61B 5/6852*
        (2013.01); *A61B 5/6878* (2013.01); *A61B*
        *5/742* (2013.01); *A61B 17/3403* (2013.01);
        *A61B 2090/064* (2016.02); *A61B 2562/0247*
        (2013.01); *A61B 2562/225* (2013.01)
(58) Field of Classification Search
   CPC ......... A61B 5/742; A61B 5/743; A61B 5/065;
        A61B 5/02116; A61B 5/03; A61B
        5/6852; A61B 5/6878; A61B 17/3403;
        A61B 17/3472; A61B 2562/0247; A61B
        2562/225; A61M 25/06
   See application file for complete search history.

(56)                References Cited

U.S. PATENT DOCUMENTS

| | | | |
|---|---|---|---|
| 9,358,038 B2 | 6/2016 | Hulvershorn et al. | |
| 2005/0171504 A1* | 8/2005 | Miller | A61B 17/1671 |
| | | | 604/506 |
| 2011/0046477 A1 | 2/2011 | Hulvershorn et al. | |
| 2011/0054353 A1* | 3/2011 | Hulvershorn | A61M 25/0693 |
| | | | 600/587 |
| 2012/0271168 A1* | 10/2012 | Radojicic | A61M 25/00 |
| | | | 600/483 |
| 2016/0015893 A1 | 1/2016 | Hoyt et al. | |
| 2016/0029995 A1* | 2/2016 | Navratil | A61B 5/08 |
| | | | 600/301 |
| 2018/0078171 A1* | 3/2018 | Cruz, Jr. | A61B 5/6852 |

FOREIGN PATENT DOCUMENTS

| | | | | |
|---|---|---|---|---|
| WO | WO-2018075435 A1 * | 4/2018 | ...... | A61M 25/09041 |
| WO | 2022226509 A1 | 10/2022 | | |

OTHER PUBLICATIONS

Frascone, MD, Ralph J., et al., "Evaluation of intraosseous pressure in a hypovolemic animal model," Journal of Surgical Research, 193:383-390 (2015).
Frascone, MD, Ralph J., et al., "Use of an intraosseous device for invasive pressure monitoring in the ED," American Journal of Emergency Medicine, 32:692e3-692e4 (2014).
Greenstein, et al., "A Serious Adult Intraosseous Catheter Complication and Review of the Literature," Crit. Care Med, 44(9):e904-e909 (2016).
Greenstein, Y., MD, "Intraosseous Catheter Confirmation Study—Full Text View—ClinicalTria . . . " Available online at https://clinicaltrials.gov/ct2/show/study/NCT03908879, 7 pages, Downloaded Apr. 19, 2022.
ICUMedical, Transpac IV Disposable Pressure Transducer System, ICU Medical Inc., 2 pages, (2012). Available online at https://www.icumed.com/products/critical-care/blood-pressure-monitoring/transpac-iv, Downloaded Jul. 20, 2022.

Jacob, Avila, et al., "Trick of the Trade: Squeeze test for confirmation of IO placement," Available online at https://www.aliem.com/trick-of-the-trade-squeeze-test-for-confirmation-of-io-placement/. Aliem., 6 pages, Downloaded Jul. 15, 2022.
Landy, C., et al., "Complication of intraosseous administration of systemic fibrinolysis for a massive pulmonary embolism with cardiac arrest," Resuscitation, 83:e149 e150 (2012).
LaSpada J, Kissoon N, Melker R, Murphy S, Miller G, Peterson R. Extravasation rates and complications of intraosseous needles during gravity and pressure infusion. Crit Care Med. Dec. 1995;23(12):2023-8.
Link, MS, Berkow LC, Kudenchuck PJ, et al. 2015 American Heart Association Guidelines for Cardiopulmonary Resuscitation and Emergency Cardiovascular Care Science. Part 7: Adult Advanced Cardiovascular Life Support. Circulation 2010.
McDermott, et al., "A new method to measure intraosseous pressures," Clin. Orthop. Relat. Res., Jul:(208):25-7 (1986).
Moscati, R., and Moore, G.P., "Compartment syndrome with resultant amputation following intraosseous infusion," Am. J. Emerg. Med., 8(5):470-1 (1990).
Narasimhan, M., et al., "A Whole-Body Approach to Point of Care Ultrasound," Chest, 150(4):772-776 (2016).
Neumar, R.W., et al., "Part 8: adult advanced cardiovascular life support: 2010 American Heart Association Guidelines for Cardiopulmonary Resuscitation and Emergency Cardiovascular Care," Circulation, 122:S729-S767 (2010).
Panchal, A.R., et al., "2018 American Heart Association Focused Update on Advanced Cardiovascular Life Support Use of Antiarrhythmic Drugs During and Immediately After Cardiac Arrest an Update to the American Heart Association Guidelines for Cardiopulmonary Resuscitation and Emergency Cardiovascular Care."
Reades, R., et al., "Comparison of first-attempt success between tibial and humeral intraosseous insertions during out of-hospital cardiac arrest," Prehosp. Emerg. Care, 15:278-281 (2011).
Salzman, J.G., et al. "Intraosseous Pressure Monitoring in Healthy Volunteers," Prehosp. Emerg. Care, 21:567-574 (2017).
Santos, D., et al., "EZ-IO(®) intraosseous device implementation in a pre-hospital emergency service: A prospective study and review of the literature," Resuscitation, 84:440-445 (2013).
Strausbaugh, et al. "Circumferential pressure as a rapid method to assess intraosseous needle placement." Pediatric Emergency Care, 11(5):274-276 (1995).
Stone, M.B., et al., "Ultrasonographic confirmation of intraosseous needle placement in an adult unembalmed cadaver model," Annals of Emergency Medicine, 49(4):515-9 (2007).
Teleflex®. (2014). EZ-IO® Intraosseous Vascular Access Needles: Instructions for Use (Jul. 2015).
Tsung ,J.W., et al., "Feasibility of point-of-care colour Doppler ultrasound confirmation of intraosseous needle placement during resuscitation," Resuscitation, 80(6):665-8 (2009).
Wampler, D., et al., "aramedics successfully perform humeral EZ-IO intraosseous access in adult out-of-hospital cardiac arrest patients," Am J Emerg Med, 30:1095-1099 (2012).
International Search Report and Written Opinion for International Application No. PCT/US2022/071818, entitled "Intraosseous Catheter Placement Confirmation Device and Method," with a mailing date of Aug. 26, 2022.
International Preliminary Report on Patentability for International Application No. PCT/US2022/071818, entitled "Intraosseous Catheter Placement Confirmation Device and Method," with a mailing date of Apr. 22, 2022.

* cited by examiner

Pressure Waveform Method

| Standard Method | No | Yes | Total |
|---|---|---|---|
| No | 3 | 0 | 3 |
| Yes | 7 | 32 | 39 |
| Total | 10 | 32 | 42 |

McNemar: p < 0.01

FIG. 9A

Pressure Waveform- Blinded rev 1 vs Blinded rev 2

Blinded Rev 2

| Blinded Rev 1 | No | Yes | Total |
|---|---|---|---|
| No | 10 | 2 | 12 |
| Yes | 2 | 28 | 30 |
| Total | 12 | 30 | 42 |

Kappa statistic: 0.77

Kappa: p < 0.001

Substantial Agreement

INTRAOSSEOUS CATHETER PLACEMENT CONFIRMATION DEVICE AND METHOD

RELATED APPLICATION

This application claims the benefit of U.S. Provisional Application No. 63/178,175, filed on Apr. 22, 2021. The entire teachings of the above application are incorporated herein by reference.

BACKGROUND

Intraosseous (IO) catheters allow medical providers to rapidly administer fluids and medications to critically ill patients when intravenous (IV) access is not present or difficult to achieve. The IO catheters are recommended in the advanced cardiac life support guidelines released by the American Heart Association and are used by many clinicians in both out-of-hospital emergency care and inpatient hospital care.

SUMMARY

The present technology relates to a method and device for quick confirmation of intraosseous (IO) catheter placement. Such IO catheters are used during a medical emergency to establish vascular access and to administer medicine and fluids when IV or central line access cannot be established. Correct placement of the IO catheter is important and often needs to be determined quickly.

In an embodiment, the invention is a small sterile disposable device that connects to an IO catheter and provides a clinician with actionable information to help the clinician determine whether the catheter is placed correctly, e.g., in the medullary cavity of bone. The device uses a novel concept to provide this information leveraging the presence or absence of pulsatile pressure waveforms, e.g., arterial pressure waveforms.

In another embodiment, a method for assessing placement of an intraosseous catheter includes coupling a pressure transducer to an intraosseous catheter placed in tissue and obtaining a continuous pressure waveform from a pressure signal provided by the pressure transducer. Placement of the catheter is assessed based on the continuous pressure waveform.

Assessing the placement of the catheter can include visually inspecting the continuous pressure waveform, determining absence or presence of a pulsatile waveform in the continuous pressure waveform, determining resemblance of the continuous pressure waveform to an arterial pressure waveform, or combinations thereof.

Presence of a pulsatile waveform in the continuous pressure waveform is indicative of placement of the catheter in a medullary cavity of a bone. Absence of a pulsatile waveform is indicative of placement of the catheter in soft tissue.

Determining the presence of a pulsatile waveform in the continuous pressure waveform can include detecting a rhythmic pulsation in the continuous pressure waveform, detecting a peak pressure and a trough pressure that differ by at least 5 mmHg, or both.

The pressure transducer can be integrated into a portable device that includes a display, and obtaining the continuous pressure waveform can include displaying the continuous pressure waveform on the display.

A device for assessing placement of an intraosseous catheter includes a housing, a display integrated into the housing, a first connector at a first side of the housing to couple to an intraosseous catheter placed in tissue, an inner channel in fluid communication with the connector and within the housing, and a pressure transducer configured to sample pressure from the inner channel and to provide a pressure signal based on the sampled pressure. A processor is provided that is configured to: obtain a continuous pressure waveform from the pressure signal provided by the pressure transducer; and cause the display to display the continuous pressure waveform, wherein the displayed continuous pressure waveform is indicative of placement of the catheter in the tissue.

The presence of a pulsatile waveform in the continuous pressure waveform, e.g. in the displayed continuous pressure waveform, is indicative of placement of the catheter in a medullary cavity of a bone. The absence of a pulsatile waveform in the continuous pressure waveform, e.g., in the displayed continuous pressure waveform, is indicative of placement of the catheter in soft tissue.

The device can include a second connector at a second side of the housing, the second connector being in fluid communication with the channel within the housing. The channel can extend between the first and second connectors. The device can further include a cap to close the second connector.

A method for placing an intraosseous catheter includes placing an intraosseous catheter in tissue, coupling a pressure transducer to the intraosseous catheter placed in tissue, obtaining a continuous pressure waveform from a pressure signal provided by the pressure transducer, assessing placement of the catheter in the tissue based on the continuous pressure waveform by determining absence or presence of a pulsatile waveform in the continuous pressure waveform, and in case of absence of a pulsatile waveform, adjusting placement of the catheter in the tissue.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 9A and 9B are tables showing results of a diagnostic accuracy study to compare various methods of confirming correct placement of an intraosseous (IO) catheter.

DETAILED DESCRIPTION

A description of example embodiments follows.

Intraosseous (IO) catheters are used to deliver medicine and fluid directly into the marrow of a bone in patients of which intravenous (IV) access or central line access is not available during medical emergency. Correct placement of the IO catheter often needs to be determined quickly and reliably.

Various IO catheters are regularly used throughout the world in the pre-hospital emergency setting and inpatient hospital setting. Teleflex, the manufacturer of the EZ-IO catheter, a commonly used device in the United States, reported more than 3 million units sold as of 2017.

Figure 1:
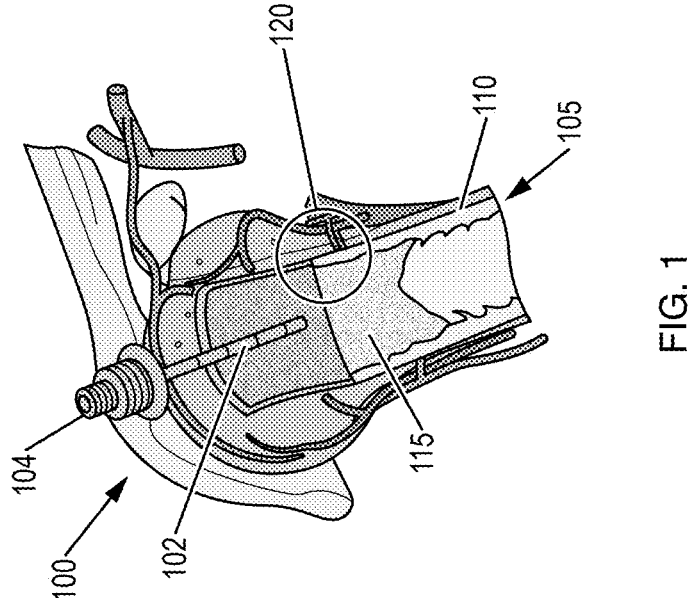
FIG. 1 illustrates an example of placement of an intraosseous (IO) catheter for intraosseous infusion.

FIG. 1 illustrates an example of placement of an intraosseous (IO) catheter for intraosseous infusion. In the example, the IO catheter 100 is placed in the proximal end of the humerus bone 105. The IO catheter 100 includes a needle 102 that is inserted through cortical bone 110 into the medullary space 115 of the bone 105. Typically, the needle is inserted with aid of a stylet (not shown), which is removed after placement of the needle in the bone. A connector 104 at a proximal end of the needle 102 is provided for connection of a fluid line. IO catheters are typically placed in the proximal and distal ends of long bones. Within the medullary space of these long bones is a system of blood vessels. These blood vessels are connected through canals in the cortical bone 110 to a arteries and veins outside the bone, as illustrated at 120.

Currently there is no convenient method of accessing the correct placement of IO catheters. A healthcare provider will typically rely on one or more of the following to determine IO catheter placement:

a) Return of bone marrow with aspiration;
b) Visualization of blood on the stylet;
c) Firm placement of the needle in the bone;
d) Ability to smoothly deliver a fluid flush;
e) Manual compression of area around the IO for checking IO flow (see, e.g., Jacob Avila et al., "Trick of the Trade: Squeeze test for confirmation of IO placement", Aliem, Jul. 22, 2015, available online at https://www.aliem.com/trick-of-the-trade-squeeze-test-for-confirmation-of-io-placement/; Strausbaugh et al. "Circumferential pressure as a rapid method to assess intraosseous needle placement." Pediatric Emergency Care 1995; 11(5):274-276).

According to clinicians that routinely place IO catheters, these currently available techniques do not provide a satisfactory method to determine correct placement. Although IO catheters are quite safe, there have been many reports of adverse events related to catheters being placed incorrectly or becoming dislodged (see, e.g., Greenstein et al. Crit Care Med 2016; 44(9):e904-e909).

The method and associated device described herein allow clinicians to better determine if the IO catheter is correctly placed. Further, clinicians can use the device to spot check the catheter for correct placement over time.

The presence of arterial waveforms in pressure measurements from IO catheters placed in humans has been described in prior research publications (see, e.g., Frascone R J et al. "Use of an intraosseous device for invasive pressure monitoring in the ED" Am J Emerg Med Jun. 1, 2014, 692.e3-692.e4, published online Dec. 19, 2013 https://doi.org/10.1016/j.ajem.2013.12.029; and Salzman J G et al. "Intraosseous Pressure Monitoring in Health Volunteers" Prehosp Emerg Care 2017; 21:567-574).

A case of successful IO pressure (IOP) monitoring through an IO device during the resuscitation of a patent has been described in Frascone et al. (Frascone R J, et. al. "Use of an intraosseous device for invasive pressure monitoring in the ED" Am J Emerg Med Jun. 1, 2014, 692.e3-692.e4). In another publication, Frascone et al. report that the intraosseous (IO) waveform most closely resembled the arterial pressure waveform, including the presence of a dichrotic notch (Frascone R J et. al. "Evaluation of intraosseous pressure in a hypovolemic animal model" Journal of Surgical Research 193(2015) 383-390).

A technique for measuring intraosseous pressures that involves inserting a miniature transducer directly into the intraosseous space has been described by McDermott et al. (McDermott A G, Yabsley R H and Leahey J L "A new method to measure intraosseous pressures" (1986) Clin. Orthop. Relat. Res. Jul; (208):25-7).

The above research publications do not discuss the use of an IO pressure waveform to determine correct placement of an IO catheter. Rather, these publications simply discuss the potential relationship between the intraosseous pressure and the systemic blood pressure.

Attaching a properly placed IO catheter to a pressure transducer produces a pulsatile waveform due to the presence of arteriole networks in the intraosseous space, e.g. the medullary cavity. The measurements of systolic, diastolic, and mean pressure readings from an IO catheter are variable; however, despite the variability in pressure readings there is uniformity in the production of a pulsatile waveform when the pressure transducer is attached to a properly placed IO catheter. Therefore, the ability to demonstrate a pulsatile waveform from an IO catheter confirms correct IO placement as objective data is being recorded directly from the intraosseous space.

It should be noted that a 'pulseless' patient will not have an arterial or an IO pressure waveform. Instead, the patient will have 'flatline' waveforms. In such a patient, assessing placement of the IO catheter based on continuous pressure waveform analysis is not expected to be successful and another approach to confirm placement of the IO catheter should be used.

Figure 2:
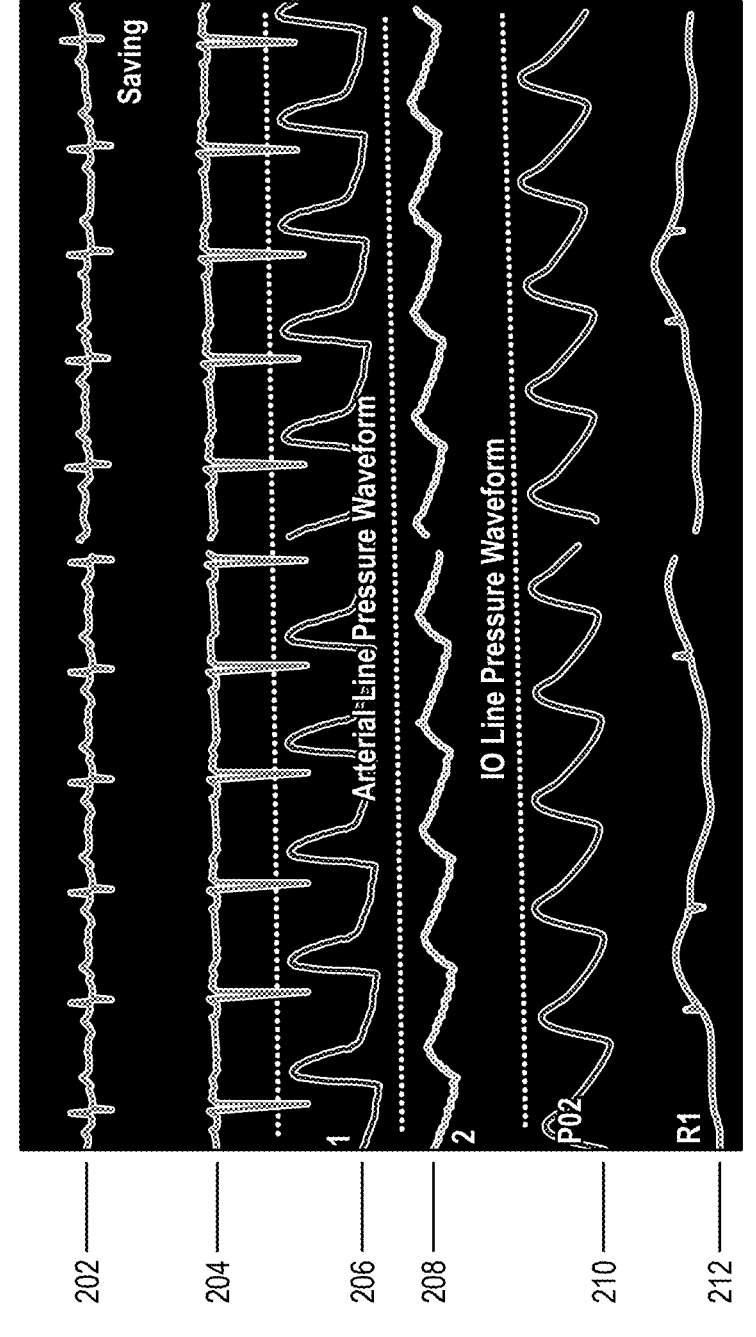
FIG. 2 illustrates an example of an arterial line pressure waveform and a correctly placed IO line pressure waveform.

FIG. 2 illustrates an example of an arterial line pressure waveform and an IO line pressure waveform displayed concurrently on a patient monitor along with other vital signs. The display 200 shows, from top to bottom, first and second ECG waveforms 202, 204, a radial arterial line pressure waveform 206, an IO line pressure waveform 208, an oxygen saturation (SPO$_2$) waveform 210, and a respiratory rate waveform 212. Here, the IO pressure waveform 208 visually resembles the arterial line pressure waveform 206. When an IO catheter is correctly placed within the medullary space, an arterial pressure waveform is evident when the catheter is transduced using a standard pressure transducer. A typical pressure transducer that can provide this useful information is cumbersome to set up and requires an experienced nurse and specialized bedside monitor. The ICUMedical Transpac IV device (https://www.icumed.com/products/critical-care/blood-pressure-monitoring/transpac-iv) is an example of a disposable pressure transducer that can be used to measure IO pressure, but the setup is complicated and time consuming, which can pose a risk in emergency situations.

The disclosed technology relates to a quick and reliable method of accessing the correct placement of an IO catheter. A disposable pressure transducer is connected to an IO catheter, calibrated for use in the intraosseous space, and used to provide a continuous IO pressure waveform. When such a waveform resembles an arterial waveform, it indicates the correct placement of the IO catheter.

Figure 3:
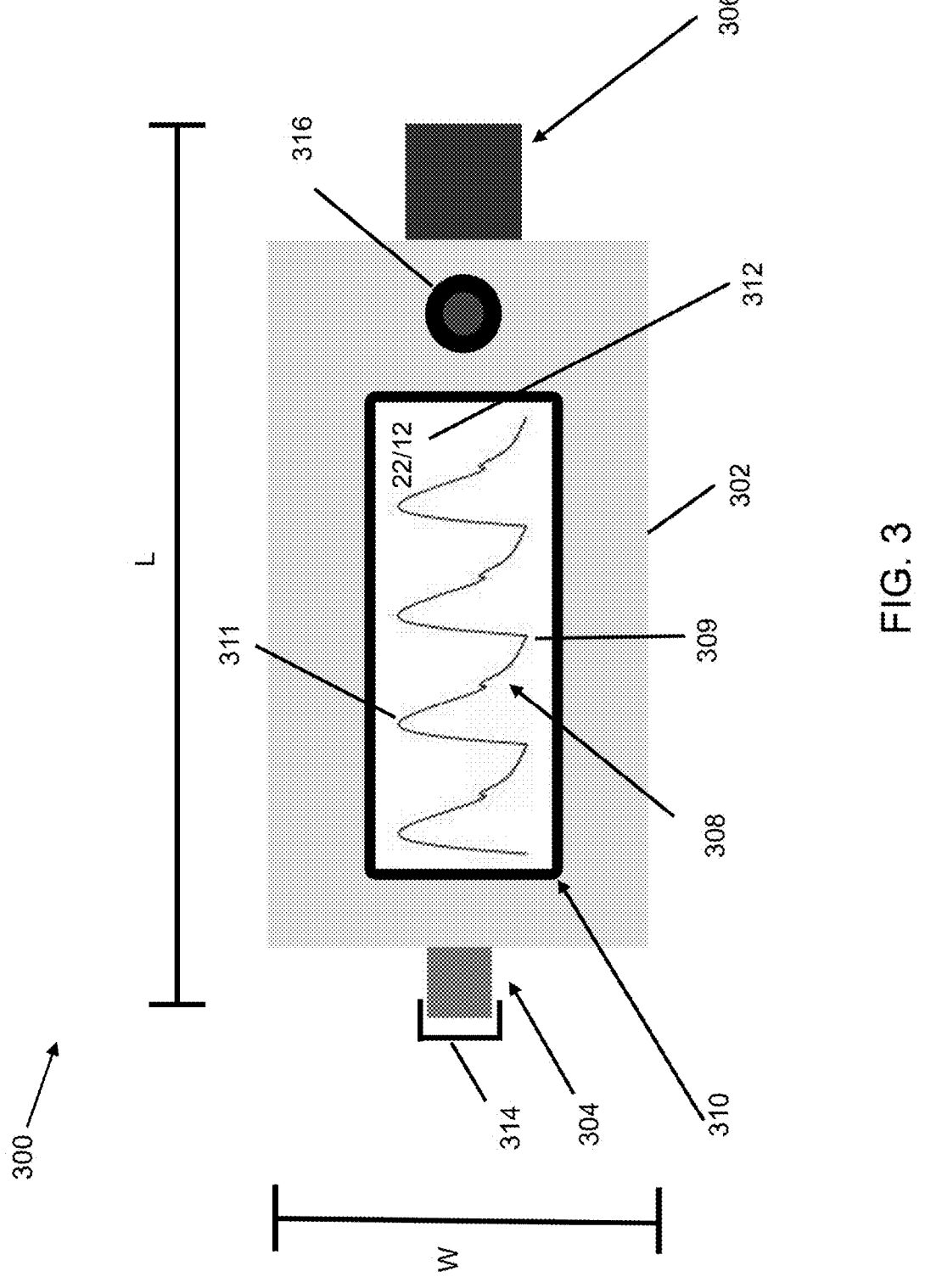
FIG. 3 schematically illustrates an external view of an example device for assessing placement of an IO catheter.

FIG. 3 schematically illustrates an external view of an example device 300 for assessing placement of an IO catheter. The device 300 includes a housing 302 having two connection ports (e.g. first and second connectors), a female Luer lock tip connection 304 and a male Luer lock tip connection 306, and a digital display 310 to display, e.g., in real-time, a pressure waveform 308 derived from an internal pressure transducer (see 424, FIG. 4). Here, the illustrated waveform 308 resembles arterial waveform. The waveform includes a peak pressure 311 and a trough pressure 309. Typically, a difference in pressure is at least 5 mmHg between peak and trough pressures is indicative of a pulsatile waveform. In addition, the actual pressure measured by the transducer can also be displayed numerically in the display. As illustrated at 312, the display can show the pressure measurement as a systolic pressure, here 22 mmHg, and a diastolic pressure, here 12 mmHg. The display 310 can be a touch sensitive display to allow for user input, for example, to adjust display parameters, such as vertical and horizontal scaling of the displayed waveform, or to pause or reset the display, etc.

A power button 316 is provided to turn the device on or off and can include a 60-second auto off feature. The female Luer lock connection 304 is provided with a removable cap 314. During pressure measurements, when the device 300 is coupled to the IO catheter via the male Luer lock tip connection 306, the female Luer lock connection 304 is capped using the cap 314 or, alternatively, a syringe (no shown) can be attached to the female Luer lock connection. The device is sized to be small and portable. In the illustrated example, the device has a length dimension L and a width dimension W. For example, L can be about 2.5 inches and W can be about 1.125 inches. The device 300 can be a sterile, single-use device, but may be used multiple times on the same patient.

Figure 4:
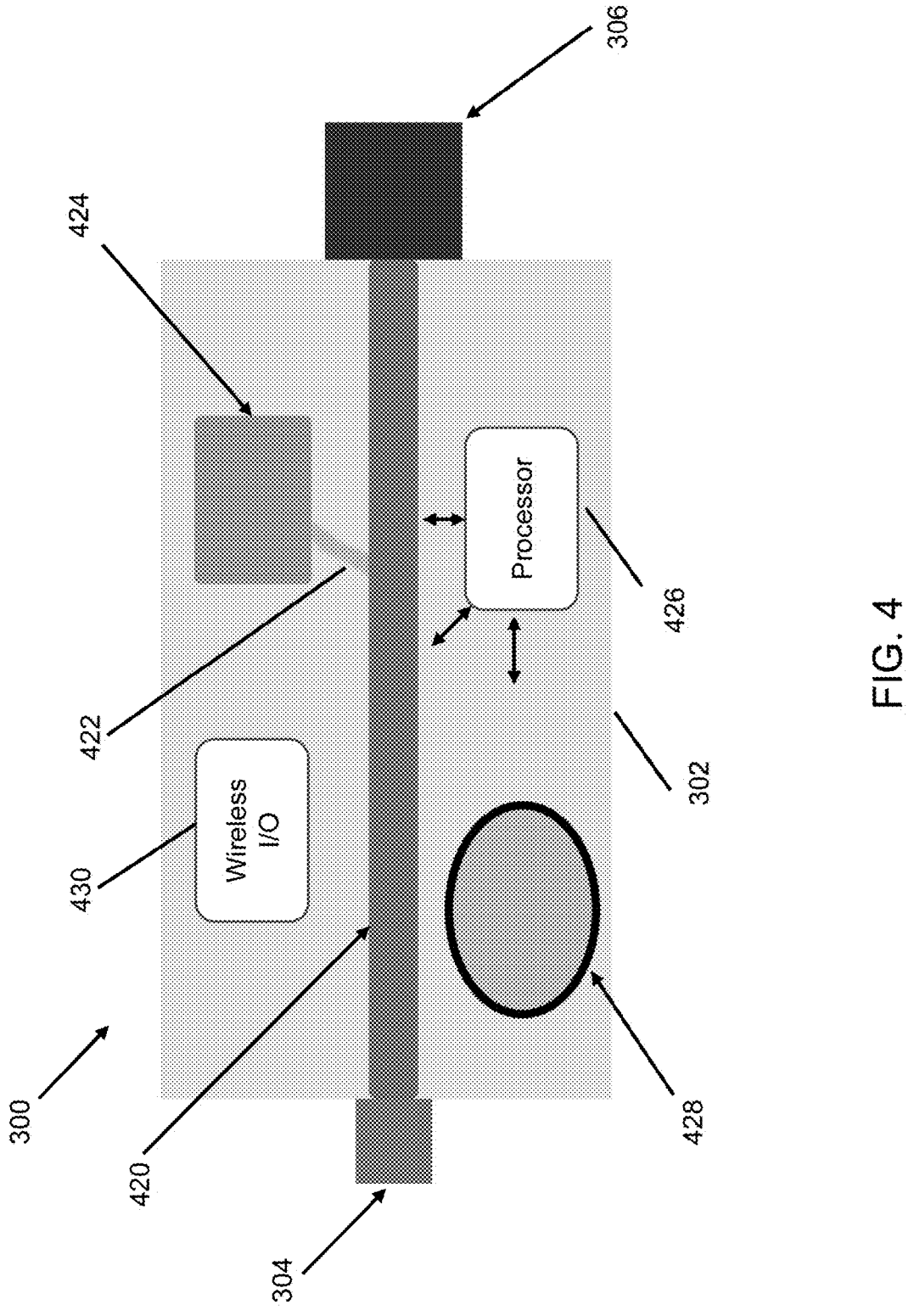
FIG. 4 schematically illustrates an internal view the example device of FIG. 3.

FIG. 4 schematically illustrates an internal view of the example device 300 of FIG. 3. As shown, the device includes an inner channel 420 continuous between the female 304 and male 306 Luer lock connections. A pressure transducer 424 samples pressure from the inner channel 420 via an interface 422. The device includes electronics, e.g., a processor 426, configured to receive a pressure signal from the transducer 424 and to drive the display 310 (FIG. 3), to display a pressure waveform based on the received pressure signal. The processor can be configured to adjust the display of the waveform automatically or in response to user input. The processor is operatively connected to other components of the device, including memory storage, the display 310, the power button 316, the pressure transducer 424, and a wireless input/output (I/O) module 430. The wireless module 430 is configured to send and receive data wirelessly via a suitable wireless network/communications protocol, such as WIFI or BLUETOOTH. A power source 428, e.g. a battery, powers the electronics, including the processor, the pressure transducer, the wireless module, and the display.

The assessment of placement of the catheter is visual, and can be done by the clinician. An automatic analysis is contemplated. The clinician can look for the presence of a pulsatile waveform. The clinician can make the determination based only on the IO pressure waveform and does not need a concurrent arterial waveform to be present. If the catheter is not placed correctly, i.e., not in the medullary space of the bone, the device will not display a pulsatile waveform. The clinician would then need to adjust placement of the IO catheter or remove the IO catheter and place another catheter.

Advantageously, the pressure transducer can be calibrated for use in the intraosseous space. Based on literature and clinical experience, an adequate pressure range is believed to be 20 mmHg to 60 mmHg. A wider range can be used, e.g. 0 mmHg to 120 mmHg. If the wider range is used, the device (e.g., the processor) preferably can adjust the scale of the waveform displayed on the display automatically, e.g., based on peak pressure of the waveform, or in response to user input, e.g., via a button or a user interface, so that the user can deduce the presence or absence of a pulsatile waveform. If the scale is too large, the waveform will appear non-pulsatile (i.e. flat).

Embodiments of the present invention may be similar in size and connection interfaces to a commercially available transducer device called COMPASS (http://compass.centurionmp.com/, manufactured by Centurion Medical Products), which is a small, portable, single use pressure transducer. That device includes a male Luer lock tip connection, a female Luer lock tip connection including a cap. Its weight is 16 grams. The COMPASS device is marketed for use with central line insertion, lumbar puncture, thoracentesis, and to monitor the pressure of a compartment. The device is easy to use, but it does not provide a pressure waveform. The COMPASS device displays numerical pressure that represents a 3-second average pressure, which is updated two times per second. In contrast, the present approach provides a continuous waveform display that updates significantly faster, e.g., in real-time.

The present device includes a pressure transducer calibrated for use in the intraosseous space. Instead of providing the clinician solely with a numerical pressure measurement, the device includes a display to provide the clinician with a continuous pressure waveform based on the measured pressure. The clinician can inspect the waveform to determine if it is, or resembles, an arterial waveform signifying correct placement of the catheter in bone.

Figure 5:
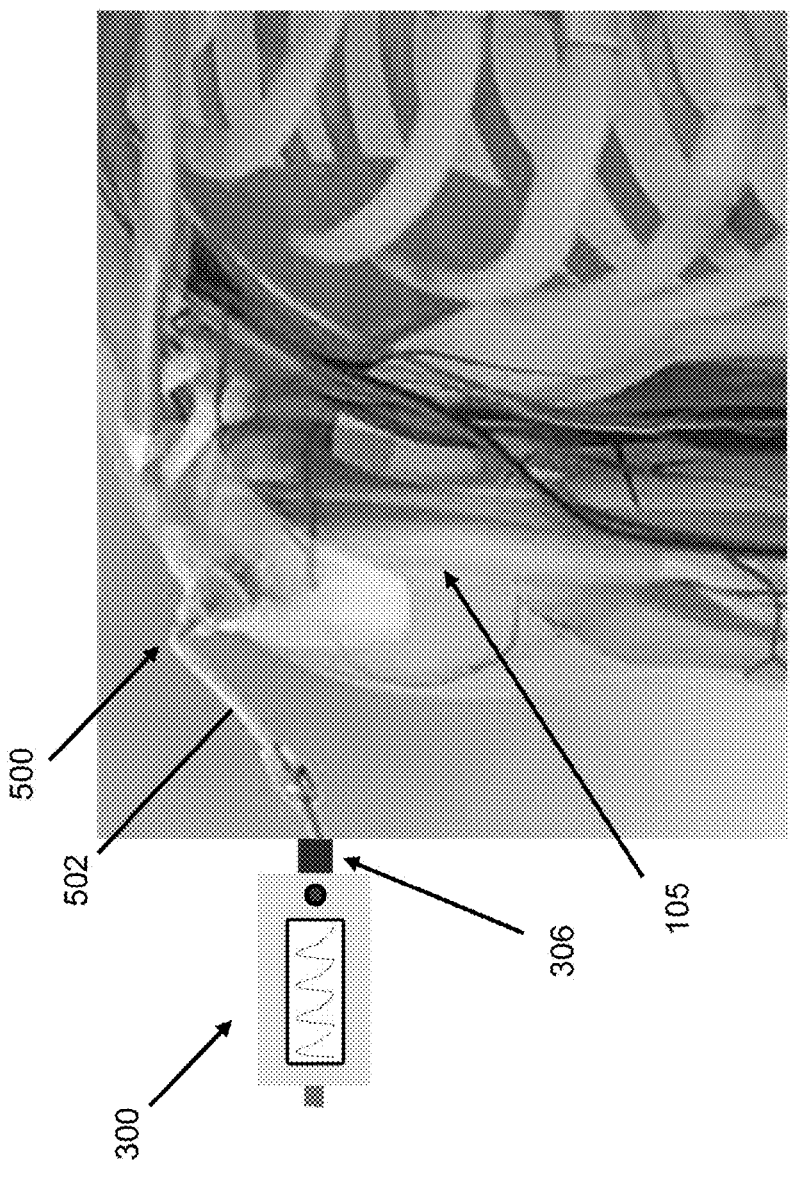
FIG. 5 illustrates connection of an example device to an IO catheter placed in bone.

FIG. 5 illustrates an example disposable pressure transducer device 300 connected to an IO catheter 500 placed in a long bone 105. The disposable pressure transducer device is connected, via a Luer lock connection 306, to a tubing 502 of the IO catheter, calibrated for use in the intraosseous space, and used provide a continuous IO pressure waveform. When such a waveform resembles an arterial waveform, it indicates the correct placement of the IO catheter. The disclosed technology provides a quick and reliable method of accessing the correct placement of an IO catheter.

Figure 6:
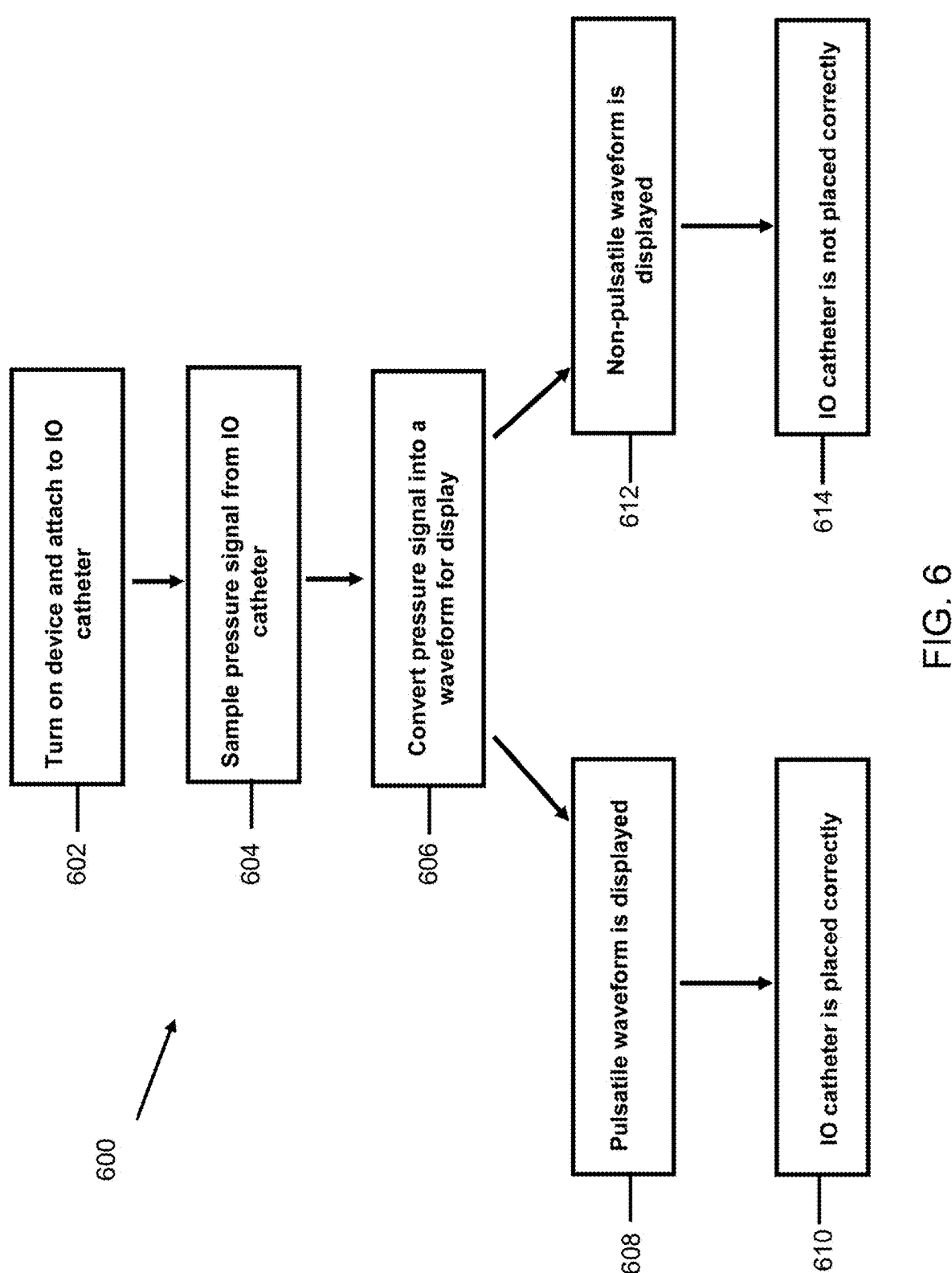
FIG. 6 is a flow chart of an example process of displaying and interpreting a pressure waveform for assessment of placement of an IO catheter.

FIG. 6 is a flow chart 600 of an example process of displaying and interpreting a pressure waveform for assessment of placement of an IO catheter. At 602, a clinician turns on the device and couples the device to the IO catheter, e.g. by coupling a Luer lock connector of the device to a corresponding connector of the IO catheter. At 604, the device senses analog pressure from the IO catheter. At 606, the device converts the analog pressure signal into a waveform for display on the device. Next, the displayed waveform can be assessed. If the displayed waveform is a pulsatile waveform (608), this is an indication that the IO catheter is correctly placed (610). If the displayed waveform is a non-pulsatile waveform (612), this is an indication that the IO catheter is not correctly placed (614). In the case that the IO catheter is not correctly placed, the clinician can reposition the IO catheter. The process can repeat from step 604 until correct placement is achieved.

7 8

Figures 7, 8:
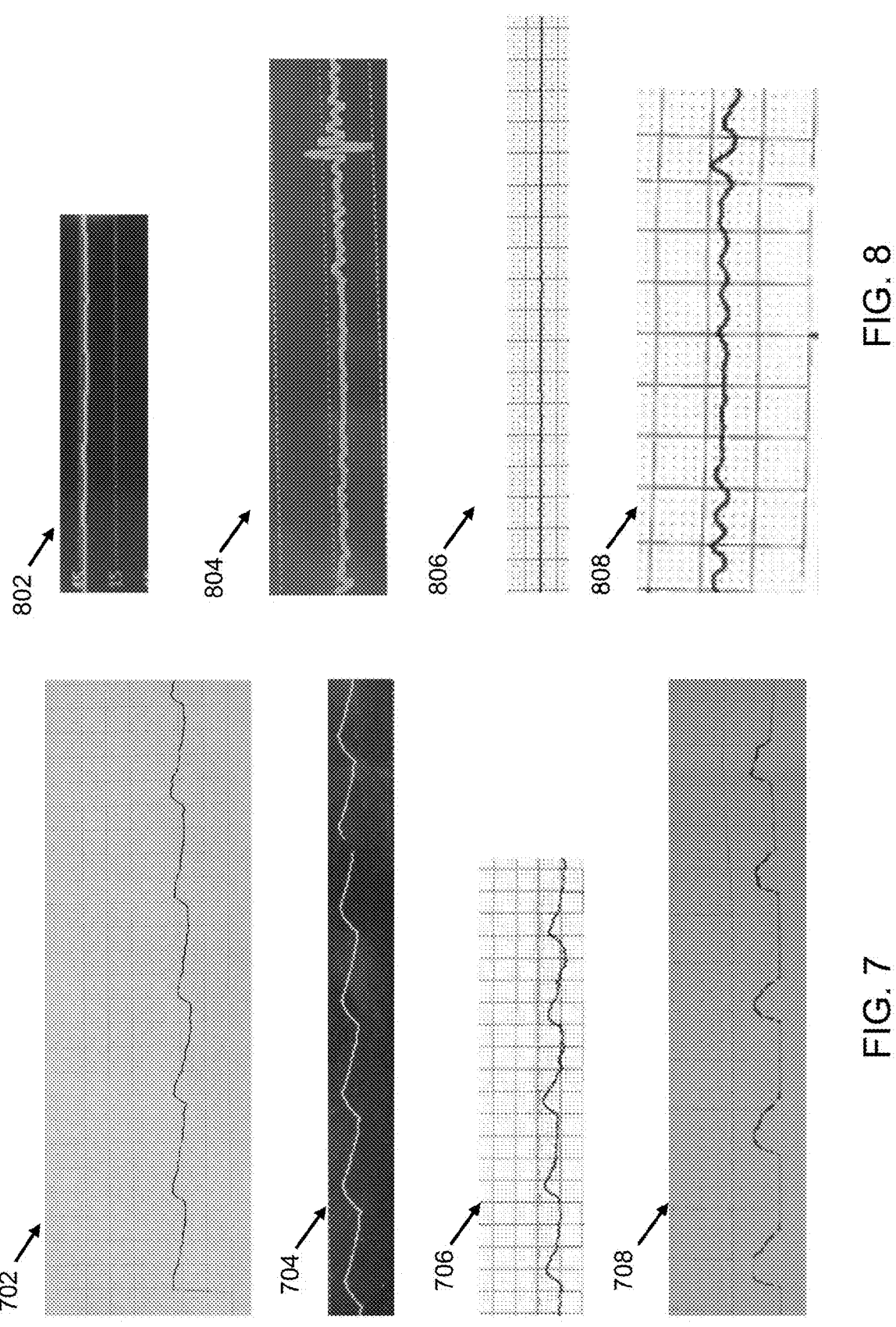
FIG. 7 illustrates several examples of pulsatile waveforms (signifying a correctly placed IO catheter).
FIG. 8 illustrates several examples of non-pulsatile waveforms (signifying an incorrectly placed IO catheter).

FIG. 7 illustrates several examples of pulsatile waveforms 702, 704, 706, and 708, which were obtained, in each case, from an IO catheter. Each of the waveforms is pulsatile, e.g., it is characterized by a rhythmic pulsation, such as regular spaced peaks and troughs, signifying a catheter that was placed correctly within the intraosseous space.

FIG. 8 illustrates several examples of non-pulsatile waveforms 802, 804, 806, and 808, signifying an incorrectly placed IO catheter. The waveforms are from IO catheters that were not placed correctly and were within soft tissue, but not the intraosseous space.

FIGS. 9A and 9B are tables showing results of a diagnostic accuracy study to compare various methods of confirming correct placement of an intraosseous (IO) catheter. As summarized in the table of FIG. 9A, the analysis shows that of 4210 catheter insertions, 24% of IO catheters were misplaced. The pressure waveform analysis technique identified all of them, whereas the standard technique identified just 30% (McNemar p<0.01) of the incorrectly placed catheters. The study employed a categorical determination (yes/no) of correct IO catheter placement. For the standard technique, the IO catheter was considered placed correctly (yes) if the physician placing the IO catheter answered "yes" to numbers 1, 2 and 3:

1. The IO catheter is able to stand upright unassisted: yes or no;

2. Bone marrow or blood is aspirated with a syringe attached to the IO catheter: yes or no;

3. There is no visible or palpable extravasation around the IO catheter site when it is flushed with a 10 mL prefilled normal saline syringe: yes or no.

For the waveform analysis technique, the IO catheter was considered placed correctly (yes) if the physicians saw a pulsatile waveform on the monitor displaying the pressure waveform from the IO catheter with numerical values for systolic pressure, diastolic pressure and a mean pressure while the IO catheter is being transduced.

The results summarized in the table of FIG. 9B show that interrater reliability of the pressure waveform technique was substantial, where agreement of incorrect placement was 10 out of 12 cases and agreement of correct placement was 28 out of 30 cases (Kappa statistic: 0.77, p<0.001).

The above results are unpublished results from an intraosseous catheter confirmation study that is registered as clinical trial NCT03908879. Additional information about the study can be found at clinicaltrials.gov (available online at clinicaltrials.gov/ct2/show/NCT03908879; accessed Apr. 19, 2022).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method for assessing placement of an intraosseous catheter, the method comprising:

coupling a pressure transducer to the intraosseous catheter placed in tissue;

obtaining a continuous pressure waveform from a pressure signal provided by the pressure transducer; and assessing placement of the catheter in the tissue based on the continuous pressure waveform, wherein assessing the placement of the catheter includes determining resemblance of the continuous pressure waveform to an arterial pressure waveform.

2. The method of claim 1, wherein assessing the placement of the catheter includes visually inspecting the continuous pressure waveform.

3. The method of claim 1, wherein assessing the placement of the catheter includes determining absence or presence of a pulsatile waveform in the continuous pressure waveform.

4. The method of claim 3, wherein the presence of the pulsatile waveform in the continuous pressure waveform is indicative of placement of the catheter in a medullary cavity of a bone, and wherein absence of the pulsatile waveform is indicative of placement of the catheter in soft tissue.

5. The method of claim 3, wherein determining the presence of the pulsatile waveform in the continuous pressure waveform includes detecting a rhythmic pulsation in the continuous pressure waveform.

6. The method of claim 3, wherein determining the presence of the pulsatile waveform in the continuous pressure waveform includes detecting a peak pressure and a trough pressure that differ by at least 5 mmHg.

7. The method of claim 1, wherein the pressure transducer is integrated into a portable device that includes a display, and wherein obtaining the continuous pressure waveform includes displaying the continuous pressure waveform on the display.

8. The method of claim 7, wherein the pressure transducer is coupled to the intraosseous catheter via a connector of the portable device, the connector being in fluid communication with an inner channel of the portable device, the pressure transducer configured to sample pressure from the inner channel to provide the pressure signal.

9. A method for placing an intraosseous catheter, the method comprising:

placing the intraosseous catheter in tissue;

coupling a pressure transducer to the intraosseous catheter placed in tissue;

obtaining a continuous pressure waveform from a pressure signal provided by the pressure transducer;

assessing placement of the catheter in the tissue based on the continuous pressure waveform by determining absence or presence of a pulsatile waveform in the continuous pressure waveform, wherein assessing the placement of the catheter includes determining resemblance of the continuous pressure waveform to an arterial pressure waveform; and in case of absence of the pulsatile waveform, adjusting placement of the catheter in the tissue.

10. The method of claim 9, wherein the pressure transducer is integrated into a portable device that includes a display, and wherein obtaining the continuous pressure waveform includes displaying the continuous pressure waveform on the display.

11. The method of claim 10, wherein the portable device includes a connector in fluid communication with the pressure transducer, wherein coupling the pressure transducer to the intraosseous catheter includes coupling the connector directly to the intraosseous catheter.

12. The method of claim 9, wherein assessing the placement of the catheter includes visually inspecting the continuous pressure waveform.

13. The method of claim 9, wherein the presence of the pulsatile waveform in the continuous pressure waveform is indicative of placement of the catheter in a medullary cavity of a bone, and wherein absence of the pulsatile waveform is indicative of placement of the catheter in soft tissue.

14. The method of claim 9, wherein determining the presence of the pulsatile waveform in the continuous pressure waveform includes detecting a rhythmic pulsation in the continuous pressure waveform.

15. The method of claim 9, wherein determining the presence of the pulsatile waveform in the continuous pressure waveform includes detecting a peak pressure and a trough pressure that differ by at least 5 mmHg.

* * * * *